United States Patent
Jikyo et al.

(10) Patent No.: US 7,485,646 B2
(45) Date of Patent: Feb. 3, 2009

(54) SEROTONIN 5-HT3 RECEPTOR AGONIST

(75) Inventors: Tamaki Jikyo, Kanagawa (JP); Koichi Shudo, Tokyo (JP)

(73) Assignee: Research Foundation Itsuu Laboratory, Tokyo (JP)

( * ) Notice: Subject to any disclaimer, the term of this patent is extended or adjusted under 35 U.S.C. 154(b) by 0 days.

(21) Appl. No.: 11/574,794

(22) PCT Filed: Sep. 8, 2005

(86) PCT No.: PCT/JP2005/016489

§ 371 (c)(1),
(2), (4) Date: May 17, 2007

(87) PCT Pub. No.: WO2006/028161

PCT Pub. Date: Mar. 16, 2006

(65) Prior Publication Data

US 2007/0265277 A1    Nov. 15, 2007

(30) Foreign Application Priority Data

Sep. 9, 2004  (JP)  ............................. 2004-298232

(51) Int. Cl.
*A61K 31/4965* (2006.01)
*A61P 1/08* (2006.01)
*C07D 241/04* (2006.01)

(52) U.S. Cl. .................. 514/255.01; 544/383; 544/390; 544/391

(58) Field of Classification Search .............. 544/383, 544/390; 514/255.01
See application file for complete search history.

(56) References Cited

U.S. PATENT DOCUMENTS

| | | | |
|---|---|---|---|
| 4,252,804 A | 2/1981 | Joullié et al. | |
| 5,631,257 A | 5/1997 | Iwamatsu et al. | |
| 6,037,342 A | 3/2000 | Sato et al. | |
| 2004/0006091 A1 | 1/2004 | Kyle et al. | |
| 2004/0044003 A1 | 3/2004 | Kyle et al. | |
| 2007/0249618 A1 * | 10/2007 | Folmer et al. | 514/252.11 |

FOREIGN PATENT DOCUMENTS

| | | | |
|---|---|---|---|
| JP | 53-135945 | * | 11/1978 |
| JP | 6-345744 | | 12/1994 |
| JP | 10-029987 | | 2/1998 |
| WO | 97/28141 | | 8/1997 |
| WO | 98/31677 | * | 7/1998 |
| WO | 03/066595 | | 8/2003 |

OTHER PUBLICATIONS

English Language Abstract of JP 10-029987.
English Language Abstract of JP 6-345744.

* cited by examiner

*Primary Examiner*—Deepak Rao
*Assistant Examiner*—Erich A Leeser
(74) *Attorney, Agent, or Firm*—Greenblum & Bernstein, P.L.C.

(57) ABSTRACT

A serotonin 5-HT3 receptor agonist containing a compound represented by the general formula (1) [$R^1$, $R^3$ and $R^5$ represent hydrogen atom, a lower alkyl group, a lower alkenyl group, a halogen atom, hydroxyl group, amino group, a lower alkoxy group, carboxyl group, carbamoyl group, or nitro group, $R^2$ and $R^4$ represent a halogen atom, hydroxyl group, or amino group, $R^6$ represents hydrogen atom, a lower alkyl group, or a lower alkenyl group, $R^7$ represents hydrogen atom, a lower alkyl group, a lower alkenyl group, or an aralkyl group, and m and n are integers of 1 to 3] or a physiologically acceptable salt thereof as an active ingredient and having both a serotonin 5-HT3 receptor antagonistic action and a serotonin 5-HT3 receptor activating action.

[Formula 1]

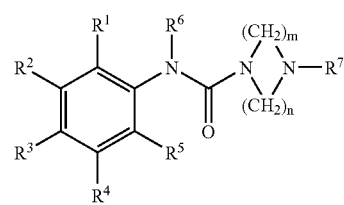

1

2 Claims, No Drawings

SEROTONIN 5-HT3 RECEPTOR AGONIST

TECHNICAL FIELD

The present invention relates to a serotonin 5-HT3 receptor agonist which comprises a urea derivative containing a quaternary salt as an active ingredient and has both a serotonin 5-HT3 receptor antagonistic action and a serotonin 5-HT3 receptor activating action. The present invention also relates to a novel urea derivative that is useful as an active ingredient of a serotonin 5-HT3 receptor agonist having the aforementioned characteristic features.

BACKGROUND ART

Emesis is a serious adverse reaction very frequently observed in patients administered with a cancer chemotherapeutic agent and patients receiving radiation therapy, and therefore, it is highly important to control emesis as an auxiliary therapy for sufficient cancer treatment. It was reported that emesis due to cancer treatment was effectively suppressed by intravenously administration of a large amount of 4-amino-5-chloro-N-[(2-diethylamino)ethyl]-2-methoxybenzamide (Non-patent document 2), which is an amide derivative developed in the middle of 1960s as an antiemetic drug or a digestive function promoting agent (nonproprietary name "metoclopramide", see, for example, Non-patent document 1), and it became possible to control emesis to a certain extent in cancer treatments. Since then, a wide variety of substituted benzoic acid amide derivatives and heterocyclic carboxylic acid amide derivatives have been synthesized and their pharmacological properties were studied [for example, Non-patent document 3 and Patent documents 1 and 2]. However, although metoclopramide suppresses mild emesis via an antagonistic action on the dopamine D2 receptor, it fails to suppress emesis caused by anticancer agents such as cisplatin at usual doses. Further, since compounds having the benzamide structure have a dopamine blocking action and a central nerve system depressing action, they cause undesirable side reactions (for example, sedation, ataxic response, diarrhea and akathisia).

The suppressing effect against cisplatin-induced emesis obtained by the administration of a large amount of metoclopramide is considered to be attributable to a serotonin 5-HT3 receptor antagonistic action [Non-patent document 4], and various serotonin 5-HT3 antagonists have been developed. These compounds having serotonin 5-HT3 receptor antagonistic action have been revealed to be effective for suppression of nausea and emesis as adverse reactions caused by anticancer agents such as cisplatin and radiotherapy, and several medicaments have been clinically used. Examples of the clinically used serotonin 5-HT3 receptor antagonists include antiemetic drugs such as ondansetron, granisetron, which is a lactam derivative, and tropisetron, which is an indole derivative [Non-patent document 5, Patent documents 3 and 4].

In the late 1970s, a benzoate derivative, MDL-72222 [Patent document 5 and Non-patent document 6], and an amide derivative, ICS 205-930 [Patent document 6 and Non-patent document 6] were discovered, which have a serotonin 5-HT3 receptor-selective antagonistic action. Since then, several benzoic acid amide derivatives and heterocyclic carboxylic acid derivatives as serotonin 5-HT3 receptor antagonists have been proposed [for example, Patent documents 7 and 8]. It has been reported that these compounds are effective for not only nausea or emesis induced by anticancer agents, migraine, arrhythmia and the like, but also schizophrenia, anxiety neurosis, dependence on alcohol, nicotine, narcotics, and the like [Patent document 9 and Non-patent document 7].

The serotonin 5-HT3 receptor abundantly exists in the vagus nerve afferent neurons in the intestinal tract, and is involved in regulations of sensation and reflex reaction in response to stimuli in the intestinal tract to greatly affect the gastrointestinal motility. Several serotonin 5-HT3 receptor antagonists as lactam derivatives are considered to be useful for the treatment of gastrointestinal disorders associated with upper intestinal motility [Patent document 10], and serotonin 5-HT3 receptor antagonists as benzamide derivatives [Patent document 11] are considered to be useful for the treatment of gastrointestinal motility disorders. Further, serotonin 5-HT3 receptor antagonists as amide derivatives having the azabicyclic system [Patent documents 10 and 12] are considered to be useful for the treatment of irritable bowel syndrome (IBS). However, these serotonin 5-HT3 receptor antagonists suffer from a problem that they cause constipation symptoms as adverse reactions. For example, it was found that "alosetron" [Patent document 13], which is a therapeutic agent for IBS as a lactam derivative, caused serious ischemic colitis and constipation as adverse reactions, and was withdrawn from the market in November 2000. Then, this medicament was reapproved under a strictly restricted use limited to female patients with diarrhea-dominant IBS.

It has been found that benzoxazole derivatives, of which development as digestive function regulating drugs is being studied, have serotonin 5-HT3 receptor antagonistic action [Patent document 14]. Further, amide derivatives having a benzoic acid skeleton disubstituted with an alkylenedioxy group in the 2nd and 3rd positions have been disclosed as serotonin 5-HT3 receptor antagonists [Patent document 15]. As described above, several antiemetic drugs and digestive function regulating drugs having the serotonin 5-HT3 receptor antagonistic action have been reported. However, none of these compounds have a urea functional group.

N-(4-Amino-5-chloro-2-methoxyphenyl)-4-benzylpiperazine-1-carboxyamide, a urea derivative of aniline, is disclosed in Patent document 16. Although this publication discloses that the aforementioned substance has a tranquilizing activity, it neither suggests nor teaches that the aforementioned substance exhibits an action selective to the serotonin 5-HT3 receptor, or that the aforementioned substance has an antiemetic action or an action on the gastrointestinal tract.

Further, N-(4,5-dichlorophenyl)-4-methylpiperazine-1-carboxyamide, a urea derivative, is known to have an antihypertensive action [Non-patent document 8], and N-(3,5-trifluoromethylphenyl)-4-methylpiperazine-1-carboxyamide is known to have an anticonvulsant action [Non-patent document 9]. However, these publications do not suggest nor teach that the aforementioned urea derivatives have an action selective to the serotonin 5-HT3 receptor, and also do not disclose that these compounds have an antiemetic action or an action on the gastrointestinal tract.

Non-patent document 1: Merck Index, 10th edition, 6019 (1983)
Non-patent document 2: N. Engl. J. Med., 305, 905 (1981)
Non-patent document 3: Ann. Rep. Med. Chem., 38, 89 (2003)
Patent document 1: U.S. Pat. No. 4,207,327, p. 2
Patent document 2: Japanese Patent Unexamined Publication (Kokai) No. 60-123485, p. 4
Non-patent document 4: Br. J. Pharmacol, 88, 497 (1986)
Non-patent document 5: Drugs of the Future, 14 (9), 875 (1989)
Patent document 3: European Patent No. 201165, p. 3
Patent document 4: European Patent No. 226226, p. 2

Patent document 5: Japanese Patent Unexamined Publication No. 58-978, p. 2
Non-patent document 6: Trends in Pharmaceutical Sciences, 8, 44 (1987)
Patent document 6: Japanese Patent Unexamined Publication No. 59-36675, p. 17
Patent document 7: Japanese Patent Unexamined Publication No. 61-275276, p. 11
Patent document 8: Japanese Patent Unexamined Publication No. 62-252764, p. 10
Patent document 9: Japanese Patent Unexamined Publication No. 1-31729, p. 4 and
Non-patent document 7: Eur. J. Pharmcol., 151, 159 (1988)
Patent document 10: European Patent No. 189002, p. 4
Patent document 11: European Patent No. 36269, p. 2
Patent document 12: European Patent No. 377967, p. 8
Patent document 13: Japanese Patent Unexamined Publication No. 1-151578, p. 6
Patent document 14: Japanese Patent Unexamined Publication No. 6-345744, p. 2
Patent document 15: International Patent Publication WO92/10494, p. 10
Patent document 16: Belgian Patent No. 866057, p. 3
Non-patent document 8: J. Med. Chem., 12, 551 (1969)
Non-patent document 9: Indian J. Chem., Sect B., 24B(9), 934 (1985)

DISCLOSURE OF THE INVENTION

Object to be Achieved by the Invention

As observed for the existing antiemetic drugs, azabicyclic type drugs, and benzamide type drugs, the administration of the compounds having only the serotonin 5-HT3 receptor antagonistic action is not satisfactorily sufficient from a viewpoint of separation of the drug efficacy and adverse reactions. Further, when the compounds having only the serotonin 5-HT3 receptor antagonistic action are administered as digestive function regulating agents, a problem arises that constipation likely occurs as an adverse reaction, although diarrhea is suppressed.

Therefore, an object of the present invention is to provide a serotonin 5-HT3 receptor agonist also having a serotonin 5-HT3 receptor activating action in addition to a serotonin 5-HT3 receptor antagonistic action, and exhibiting less severe adverse reactions caused by the serotonin 5-HT3 receptor antagonistic action compared with those observed for the conventional medicaments. Another object of the present invention is to provide a serotonin 5-HT3 receptor agonist not acting on the central nervous system, but specifically acting only on the peripheral nerve system.

Further object of the present invention is to provide a novel compound that is useful as an active ingredient of a serotonin 5-HT3 receptor agonist having the aforementioned characteristics.

Means for Achieving the Object

The inventors of the present invention conducted various researches to achieve the foregoing objects. As a result, they found that a compound represented by the following general formula (1) or a physiologically acceptable salt thereof has both a serotonin 5-HT3 receptor antagonistic action and a serotonin 5-HT3 receptor activating action, and is useful as a serotonin 5-HT3 receptor agonist exhibiting less severe adverse reactions caused by the serotonin 5-HT3 receptor antagonistic action compared with those observed for the conventional medicaments. The inventors of the present invention also found that a novel quaternary salt compound represented by the general formula (3) or a physiologically acceptable salt thereof has the aforementioned characteristics and is useful as an active ingredient of a serotonin 5-HT3 receptor agonist that does not act on the central nervous system, but specifically acts only on the peripheral nerve system. The present invention was accomplished on the basis of the aforementioned findings.

The present invention thus provides a serotonin 5-HT3 receptor agonist comprising a compound represented by the general formula (1) or a physiologically acceptable salt thereof as an active ingredient:

[Formula 1]

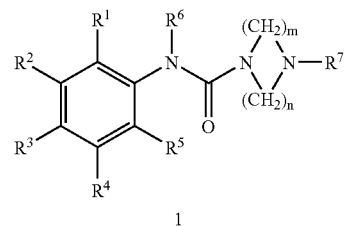

1

[wherein $R^1$, $R^3$, and $R^5$ may be the same or different, and represent hydrogen atom, a substituted or unsubstituted lower alkyl group, a substituted or unsubstituted lower alkenyl group, a halogen atom, hydroxyl group, a substituted or unsubstituted amino group, a lower alkoxy group, carboxyl group, carbamoyl group, or nitro group, $R^2$ and $R^4$ may be the same or different, and represent a halogen atom, hydroxyl group, or a substituted or unsubstituted amino group, $R^6$ represents hydrogen atom, a substituted or unsubstituted lower alkyl group, or a substituted or unsubstituted lower alkenyl group, $R^7$ represents hydrogen atom, a substituted or unsubstituted lower alkyl group, a substituted or unsubstituted lower alkenyl group, or a substituted or unsubstituted aralkyl group, and m and n may be the same and different, and represent an integer of 1 to 3].

The present invention also provides a serotonin 5-HT3 receptor agonist comprising a compound represented by the following general formula (2) or a physiologically acceptable salt thereof as an active ingredient:

[Formula 2]

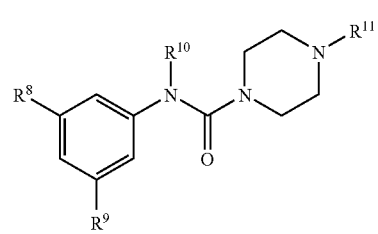

2

[wherein $R^8$ and $R^9$ may be the same or different, and represent a halogen atom, hydroxyl group, or a substituted or unsubstituted amino group, $R^{10}$ represents hydrogen atom, a substituted or unsubstituted lower alkyl group, or a substituted or unsubstituted lower alkenyl group, and $R^{11}$ represents hydrogen atom, a substituted or unsubstituted lower alkyl group, or a substituted or unsubstituted lower alkenyl group].

The serotonin 5-HT3 receptor agonist represented by the aforementioned general formula (1) or the general formula (2) has both an antagonistic action and an activating action on the serotonin 5-HT3 receptor and is useful as a serotonin 5-HT3 receptor agonist that exhibits less severe adverse reactions caused by the serotonin 5-HT3 receptor antagonistic action compared with those observed for the conventional medicaments.

The present invention further provides a compound represented by the aforementioned general formula (1) or the general formula (2) or a salt thereof (provided that a compound of the formula (1) wherein $R^2$ and $R^4$ both represent chlorine atom, a compound of the general formula (1) wherein $R^1$, $R^2$, $R^3$, $R^4$ and $R^5$ all represent chlorine atom, and a compound of the general formula (2) wherein $R^8$ and $R^9$ both represent chlorine atom are excluded).

From another aspect, the present invention also provides a compound represented by the following general formula (3):

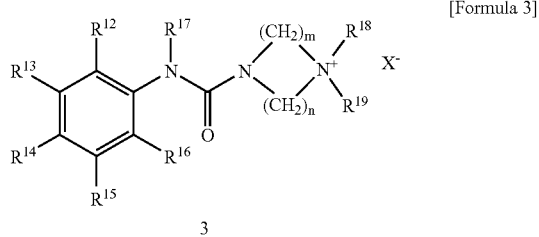

[Formula 3]

3

[wherein $R^{12}$, $R^{13}$, $R^{14}$, $R^{15}$ and $R^{16}$ may be the same or different, and represent hydrogen atom, a halogen atom, a lower alkoxy group, trifluoromethyl group, a substituted or unsubstituted lower alkyl group, a substituted or unsubstituted lower alkenyl group, or a substituted or unsubstituted amino group, any two groups among $R^{12}$, $R^{13}$, $R^{14}$, $R^{15}$ and $R^{16}$ may bind to each other to form a cyclic structure (this cyclic structure is a 5- to 7-membered cyclic structure consisting solely of carbon atoms or a 5- to 7-membered cyclic structure consisting of carbon atoms and one or two hetero atoms, and may have one or more the same or different substituents on the ring), $R^{17}$ represents hydrogen atom, a substituted or unsubstituted lower alkyl group, or a substituted or unsubstituted lower alkenyl group, $R^{18}$ and $R^{19}$ may be the same or different, and represent a substituted or unsubstituted lower alkyl group, a lower alkenyl group, or an aralkyl group, X⁻ represents a physiologically acceptable anion species, and m and n may be the same and different, and represent an integer of 1 to 3].

The present invention further provides a serotonin 5-HT3 receptor agonist comprising a compound represented by the aforementioned general formula (3) as an active ingredient. This serotonin 5-HT3 receptor agonist has both an antagonistic action and an activating action on the serotonin 5-HT3 receptor and is useful as a serotonin 5-HT3 receptor agonist exhibiting less severe adverse reactions caused by the serotonin 5-HT3 receptor antagonistic action compared with those observed for the conventional medicaments. Further, this serotonin 5-HT3 receptor agonist does not act on the central nervous system, but specifically acts only on the peripheral nerve system, and therefore, the agonist is extremely useful as a serotonin 5-HT3 receptor agonist whose adverse reactions are reduced.

From another aspect, the present invention provides use of a compound represented by the aforementioned formula (1) or the general formula (2), or a physiologically acceptable salt thereof, or a compound represented by the general formula (3) for the manufacture of the aforementioned serotonin 5-HT3 receptor agonist.

The present invention also provides use of the aforementioned serotonin 5-HT3 receptor agonist as a medicament for prophylactic and/or therapeutic treatment of a disease associated with the serotonin 5-HT3 receptor, and a method for prophylactic and/or therapeutic treatment of a disease associated with the serotonin 5-HT3 receptor, which comprises the step of administering a prophylactically and/or therapeutically effective amount of the aforementioned serotonin 5-HT3 receptor agonist to a mammal including human. Examples of the disease associated with the serotonin 5-HT3 receptor include, for example, emesis, gastrointestinal motility disorders, irritable bowel syndrome, headache, neuralgia, anxiety symptoms, depression, mental diseases, diarrhea, constipation, and the like.

EFFECT OF THE INVENTION

A serotonin 5-HT3 receptor agonist containing a compound represented by the aforementioned general formula (1) or the general formula (2) or a physiologically acceptable salt thereof, or a compound represented by the aforementioned general formula (3) as an active ingredient has both an antagonistic action and an activating action on the serotonin 5-HT3 receptor, and is useful as a potent serotonin 5-HT3 receptor agonist having reduced adverse reactions. The serotonin 5-HT3 receptor agonist provided by the present invention is characterized by a higher serotonin 5-HT3 receptor binding affinity than that of known urea derivatives having a similar structure, (N-phenyl-4-methylpiperazine-1-carboxyamide, N-(4,5-dichlorophenyl)-4-methylpiperazine-1-carboxyamide, N-(3,5-trifluoromethylphenyl)-4-methylpiperazine-1-carboxyamide, N-(3-fluorophenyl)-4-methylpiperazine-1-carboxyamide, and N-(5-chloro-2-methoxyphenyl)-(4-tert-butyloxycarbonylpiperazine)-1-carboxyamide).

BEST MODE FOR CARRYING OUT THE INVENTION

In the specification, the alkyl group, alkenyl group or aralkyl group as a whole group or a part of a group may be straight, branched, cyclic or may consist of any combination thereof. The lower alkyl group means an alkyl group having 1 to 5 carbon atoms, and the lower alkenyl group means an alkenyl group having 2 to 5 carbon atoms. Further, in the present specification, the halogen atom may be any of fluorine, chlorine, bromine and iodine.

In the general formulas (1) to (3), one or more hydrogen atoms of the alkyl group in the lower alkyl group represented by $R^1$, $R^3$, $R^5$, $R^6$, $R^7$, $R^{10}$, $R^{11}$, $R^{12}$, $R^{13}$, $R^{14}$, $R^{15}$, $R^{16}$, $R^{17}$, $R^{18}$ or $R^{19}$ may be substituted. Examples of the substituent include groups selected from the group consisting of a halogen atom, hydroxyl group, carbamoyl group, amino group and cyano group. One or more hydrogen atoms of the alkenyl group in the lower alkenyl group represented by $R^1$, $R^3$, $R^5$, $R^6$, $R^7$, $R^{10}$, $R^{11}$, $R^{12}$, $R^{13}$, $R^{14}$, $R^{15}$, $R^{16}$, $R^{17}$, $R^{18}$ or $R^{19}$ may be substituted. Examples of the substituent include groups selected from the group consisting of hydroxyl group, a halogen atom, carbamoyl group, amino group and cyano group. Examples of the substituent of the amino group represented by $R^1$, $R^2$, $R^3$, $R^4$, $R^5$, $R^8$, $R^9$, $R^{12}$, $R^{13}$, $R^{14}$, $R^{15}$ or $R^{16}$ include a straight or branched lower alkyl group, a straight or branched lower alkylcarbonyl group and a straight or branched lower alkenyl group.

In the general formula (1), preferred examples of the lower alkyl group represented by $R^1$, $R^3$ or $R^5$ include methyl group, ethyl group, n-propyl group, i-propyl group, n-butyl group, i-butyl group, t-butyl group, n-pentyl group (amyl group), i-pentyl group, neopentyl group, 1-methylbutyl group, 2-methylbutyl group, 1,1-dimethylpropyl group, 1,2-dimethylpropyl group, cyclopropyl group, cyclopropylmethyl group, and 2-hydroxyethyl group. Further, preferred examples of the lower alkenyl group represented by $R^1$, $R^3$ or $R^5$ include vinyl group, allyl group, homoallyl group, methallyl group, and crotyl group. Further, preferred examples of the substituted or unsubstituted amino group represented by $R^1$, $R^3$ or $R^5$ include amino group, an acylamino group, and an alkylamino group. The acyl group is that derived from an arbitrary carboxylic acid such as a saturated aliphatic carboxylic acid, an unsaturated aliphatic carboxylic acid, a saturated or unsaturated carbocyclic carboxylic acid, a heterocyclic carboxylic acid, a hydroxycarboxylic acid and an alkoxycarboxylic acid, and more specific examples include a lower alkanoyl group such as formyl group, acetyl group, propionyl group, butyryl group, valeryl group, i-valeryl group and pivaloyl group, an aroyl group such as benzoyl group, toluoyl group and naphthoyl group, a heteroaroyl group such as furoyl group, nicotinoyl group and i-nicotinoyl group, and the like. The acylamino group may be monosubstituted or disubstituted, and the term "alkyl" in the aforementioned examples has the same meaning as defined for the aforementioned lower alkyl group. Further, the alkylamino group may be monosubstituted or disubstituted. Preferred examples of the lower alkoxy group include methoxy group, ethoxy group, n-propoxy group and i-propoxy group.

Preferred examples of the halogen atom represented by $R^2$ or $R^4$ include chlorine atom, bromine atom and fluorine atom. Further, preferred examples of the substituted or unsubstituted amino group represented by $R^2$ or $R^4$ include the same amino groups as the aforementioned amino groups. Preferred examples of the lower alkyl group represented by $R^6$ include the same alkyl groups as the aforementioned lower alkyl groups, and preferred examples of the lower alkenyl group represented by $R^6$ include the same alkenyl groups as the aforementioned lower alkenyl groups. Preferred examples of the lower alkyl group represented by $R^7$ include the same alkyl groups as the aforementioned lower alkyl groups, and preferred examples of the lower alkenyl group represented by $R^7$ include the same alkenyl groups as the aforementioned lower alkenyl groups. Symbols m and n may be the same and different, and represent an integer of 2 or 3. The number of the halogen atoms as substituents selected from the group consisting of $R^1$, $R^2$, $R^3$, $R^4$ or $R^5$ is preferably one or two, since cytotoxicity has generally been reported for compounds containing 3 or more halogen atoms.

In the general formula (1), more preferably, $R^1$, $R^3$ and $R^5$ are selected from the group consisting of hydrogen atom, methyl group and hydroxyl group, $R^2$ and $R^4$ are independently selected from chlorine atom and methyl group, $R^6$ is hydrogen atom, and $R^7$ is methyl group or 2-hydroxyethyl group. Symbols m and n are preferably identical or different integers of 2 or 3.

However, a compound of the general formula (1) wherein $R^2$ and $R^4$ both represent chlorine atom, and a compound of the general formula (1) wherein $R^1$, $R^2$, $R^3$, $R^4$ and $R^5$ all represent chlorine atom are excluded from the compounds of the general formula (1) as the novel compounds provided by the present invention.

In the general formula (2), preferred examples of the halogen atom represented by $R^8$ or $R^9$ include chlorine atom and bromine atom. Preferred examples of the substituted or unsubstituted amino group represented by $R^8$ or $R^9$ include amino group, an acylamino group and a lower alkylamino group. The acyl group has the same meaning as that defined above. The acylamino group may be monosubstituted or disubstituted. Examples of the lower alkyl group include methyl group, ethyl group, n-propyl group, i-propyl group, n-butyl group, i-butyl group, t-butyl group, n-pentyl group (amyl group), i-pentyl group, neopentyl group, 1-methylbutyl group, 2-methylbutyl group, 1,1-dimethylpropyl group, 1,2-dimethylpropyl group, cyclopropyl group, cyclopropylmethyl group, 2-hydroxyethyl group, and the like, and the alkylamino group represented by $R^8$ or $R^9$ may be monosubstituted or disubstituted. Preferred examples of the lower alkyl group represented by $R^{10}$ include the same alkyl groups as the aforementioned lower alkyl groups, and preferred examples of the lower alkenyl group represented by $R^{10}$ include vinyl group, allyl group, homoallyl group, methallyl group and crotyl group. Preferred examples of the lower alkyl group represented by $R^{11}$ include the same alkyl groups as the aforementioned lower alkyl groups, and preferred examples of the lower alkenyl group represented by $R^{11}$ include the same alkenyl groups as the aforementioned lower alkenyl groups.

In the general formula (2), more preferably, $R^8$ and $R^9$ both represent chlorine atom, fluorine atom or methyl group, $R^{10}$ is hydrogen atom, and $R^{11}$ is methyl group or 2-hydroxyethyl group.

However, a compound of the general formula (2) wherein $R^8$ and $R^9$ both represent chlorine atom is excluded from the compounds of the general formula (2) as the novel compounds provided by the present invention.

In the general formula (3), preferred examples of the halogen atom represented by $R^{12}$, $R^{13}$, $R^{14}$, $R^{15}$ or $R^{16}$ include chlorine atom, bromine atom and fluorine atom. Further, preferred examples of the lower alkoxy group represented by these groups include methoxy group, ethoxy group, n-propoxy group and isopropoxy group. Further, preferred examples of the lower alkyl group represented by those groups include methyl group, ethyl group, n-propyl group, i-propyl group, n-butyl group, i-butyl group, t-butyl group, n-pentyl group (amyl group), i-pentyl group, neopentyl group, 1-methylbutyl group, 2-methylbutyl group, 1,1-dimethylpropyl group, 1,2-dimethylpropyl group, cyclopropyl group, cyclopropylmethyl group and 2-hydroxyethyl group. Further, preferred examples of the unsubstituted lower alkenyl group represented by those groups include vinyl group, allyl group, homoallyl group, methallyl group and crotyl group.

Preferred examples of the substituted or unsubstituted amino group represented by those groups include amino group, an acylamino group and a lower alkylamino group, and the "acyl group" herein referred to has the same meaning as defined above. The acylamino group may be monosubstituted or disubstituted. Further, preferred examples of the lower alkyl group include the same alkyl group as the aforementioned lower alkyl groups. The lower alkylamino group may be monosubstituted or disubstituted. Further, preferred examples of the cyclic structure represented by those groups include 1-naphthyl group, 2-naphthyl group, anthryl group, phenanthryl group, indanyl group, 3,4-methylenedioxyphenyl group, and the like.

Preferred examples of the lower alkyl group represented by $R^{17}$ include the same alkyl groups as the aforementioned lower alkyl groups, and preferred examples of the lower alkenyl group represented by $R^{17}$ include the same alkenyl groups as the aforementioned lower alkenyl groups. Preferred examples of the lower alkyl group represented by $R^{18}$ or $R^{19}$ include the same alkyl groups as the aforementioned lower alkyl groups, and preferred examples of the lower alkenyl group represented by $R^{18}$ or $R^{19}$ include the same alkenyl groups as the aforementioned lower alkenyl groups. Examples of the physiologically acceptable anion species represented by $X^-$ include a halogen ion, and preferred examples thereof include chlorine ion, bromine ion and fluorine ion. Further, m and n are preferably the same or different integers of 1 to 3.

In the general formula (3), more preferably, $R^{12}$, $R^{13}$, $R^{14}$, $R^{15}$ and $R^{16}$ independently represent hydrogen atom, chlorine atom, bromine atom, fluorine atom, methoxy group, trifluoromethyl group, or methyl group, and $R^{17}$ is hydrogen atom. More preferably, $R^{18}$ and $R^{19}$ independently represent methyl group, n-propyl group, cyclopropylmethyl group, 2-hydroxyethyl group, allyl group, or benzyl group. $X^-$ is more preferably chlorine ion, bromine ion, or iodine ion. Symbols m and n are preferably the same or different integers of 2 or 3.

Although the compound represented by the general formula (1) can be prepared by various methods, the compound can generally be prepared by the following two typical methods.

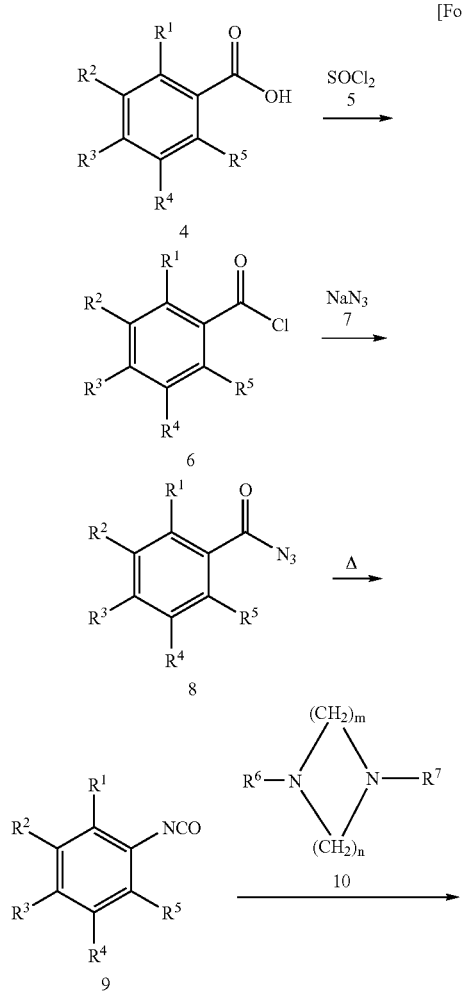

[Formula 4]

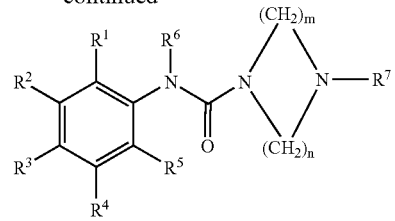

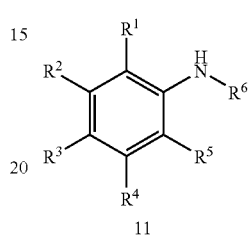

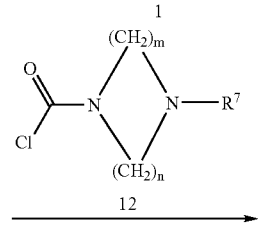

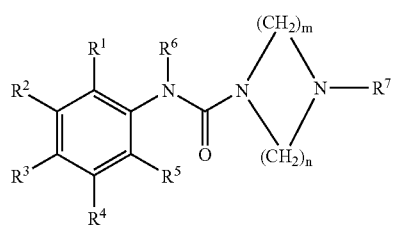

The objective compound represented by the general formula (1) can be obtained by reacting a compound represented by the general formula (9) [wherein $R^1$, $R^2$, $R^3$, $R^4$ and $R^5$ have the same meanings as those defined above] with 1 to 10 equivalents of an amine represented by the general formula (10) [wherein $R^6$, $R^7$, m and n have the same meanings as those defined above].

Alternatively, the compound represented by the general formula (1) can be obtained by reacting a compound represented by the general formula (11) [wherein $R^1$, $R^2$, $R^3$, $R^4$, $R^5$ and $R^6$ have the same meanings as those defined above] with 1 to 10 equivalents of an acid chloride represented by the general formula (12) [wherein $R^7$, m and n have the same meanings as those defined above]. The compound represented by the general formula (2) can be prepared in a similar manner.

The compound represented by the general formula (4) can be easily converted into the compound represented by the general formula (6) by allowing a chlorinating agent such as thionyl chloride to act on the compound represented by the general formula (4) at 0 to 150° C. for 1 to 12 hours. Further, the compound represented by the general formula (6) can be easily converted into the compound represented by the general formula (9) by allowing sodium azide to react on the compound represented by the general formula (7) in a solvent such as acetone at 0 to 150° C. for 1 to 12 hours to convert it into the compound represented by the general formula (8) and further reacting the compound represented by the general formula (8) in a solvent such as toluene with heating at 50 to 150° C. for 1 to 24 hours. The reaction between the compound represented by the general formula (9) and the compound represented by the general formula (10) usually rapidly advances under an anhydrous condition in a solvent such as dichloromethane at temperature of 0 to 120° C. The reaction between the compound represented by the general formula (11) and the compound represented by the general formula (12) usually rapidly advances in a solvent such as dichloromethane at temperature of 0 to 120° C. in the presence of an alkylamine base such as triethylamine.

The compound represented by the general formula (3) can be prepared by the following method.

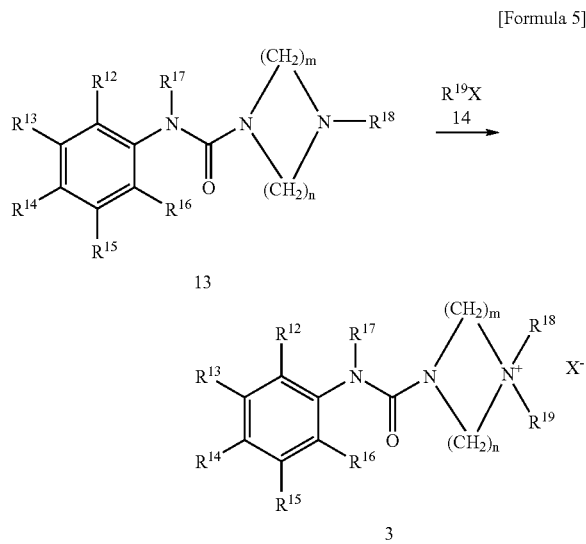

Specifically, the objective compound of the formula (3) can be obtained by reacting a compound represented by the general formula (13) [wherein $R^{12}$, $R^{13}$, $R^{14}$, $R^{15}$, $R^{16}$, $R^{17}$, $R^{18}$, m and n have the same meanings as those defined above], which can be obtained in the same manner as that used for the compound represented by the general formula (1), with a compound represented by the general formula (14) [wherein $R^{19}$ has the same meaning as defined above, and X represents a halogen atom]. For example, the compound represented by the general formula (3) can be easily obtained by reacting a compound represented by the general formula (13) and a compound represented by the general formula (14) in a solvent such as tetrahydrofuran at temperature of 0 to 80° C. for 1 to 5 hours.

The compounds represented by the general formulas (1) to (3) are useful as an active ingredient of a serotonin 5-HT3 receptor agonist having a serotonin 5-HT3 receptor activating action in addition to a serotonin 5-HT3 receptor antagonistic action (action of a serotonin 5-HT3 receptor agonist having the aforementioned characteristics may also be referred to as a serotonin 5-HT3 receptor partially activating action). Therefore, the serotonin 5-HT3 receptor agonist of the present invention can be used as a medicament for prophylactic and/or therapeutic treatment of a disease associated with the serotonin 5-HT3 receptor. Examples of the disease associated with the serotonin 5-HT3 receptor include emesis caused by anticancer agents such as cisplatin and radiation irradiation, nausea or emesis caused by kinetosis such as motion sickness, gastrointestinal motility disorders, irritable bowel syndrome, headache, neuralgia, anxiety symptom, depression, mental diseases, and the like. Further, the compound represented by the general formula (3) has the aforementioned characteristics as well as a characteristic feature that the compound does not pass through the blood-brain barrier, because of being a quaternary salt, and thus the compound is useful as an active ingredient of a serotonin 5-HT3 receptor agonist that does not act on the central nervous system, but specifically acts only on the peripheral nerve system. More specifically, the compound specifically acts on the peripheral vagus nerve system of the intestinal tract, and is useful as an antiemetic drug that suppresses symptoms such as nausea and emesis without adverse reactions on the central nervous system, particularly in the prophylactic and/or therapeutic treatment of emesis caused by administration of an anticancer agent or radiation irradiation. Further, the serotonin 5-HT3 receptor agonist of the present invention can avoid constipation as an adverse reaction of serotonin 5-HT3 receptor antagonists, and can be used as a medicament for prophylactic and/or therapeutic treatment of gastrointestinal motility regulation.

The compound represented by the general formula (1) or (2) can be used in the form of a free base or a physiologically acceptable salt thereof as an active ingredient of the serotonin 5-HT3 receptor agonist of the present invention. For example, the compound represented by the general formula (1) or (2) can also be used in the form of an appropriate acid addition salt. Examples of such a salt include a physiologically acceptable nontoxic salt, and preferred examples thereof include a salt of a hydrohalide acid such as hydrofluoric acid, hydrochloric acid, hydrobromic acid and hydroiodic acid, an inorganic acid salt such as sulfate, nitrate, phosphate, perchlorate and carbonate, a salt of a carboxylic acid such as acetic acid, trichloroacetic acid, trifluoroacetic acid, hydroxyacetic acid, lactic acid, citric acid, tartaric acid, oxalic acid, benzoic acid, mandelic acid, butyric acid, maleic acid, propionic acid, formic acid and malic acid, a salt of an acidic amino acid such as aspartic acid and glutamic acid, a salt of an organic acid such as methanesulfonic acid and p-toluenesulfonic acid, and the like. Further, the compound of the present invention represented by the general formula (3) is administered as a salt of an anion species represented by $X^-$ in the general formula (3), preferably a salt of an anion of a halogen such as chlorine, bromine and iodine.

Preferred examples of the active ingredient of the serotonin 5-HT3 receptor agonist of the present invention include:
N-(2-methylphenyl)-4-methylpiperazine-1-carboxyamide;
N-(3-methylphenyl)-4-methylpiperazine-1-carboxyamide;
N-(2-hydroxyphenyl)-4-methylpiperazine-1-carboxyamide;
N-(5-chloro-2-hydroxyphenyl)-4-methylpiperazine-1-carboxyamide;
N-(2-methylphenyl)-4-methylhomopiperazine-1-carboxyamide;
N-(3-methylphenyl)-4-methylhomopiperazine-1-carboxyamide;
N-(2-hydroxyphenyl)-4-methylhomopiperazine-1-carboxyamide;
N-(5-chloro-2-hydroxyphenyl)-4-methylhomopiperazine-1-carboxyamide;
N-(3,5-dimethylphenyl)-4-methylhomopiperazine-1-carboxyamide;
N-(3,5-dichlorophenyl)-4-methylhomopiperazine-1-carboxyamide;
N-(3,5-dichlorophenyl)-4-propylhomopiperazine-1-carboxyamide;
N-(3,5-dichlorophenyl)-4-cyclopropylmethylhomopiperazine-1-carboxyamide:
N-(3,5-dichlorophenyl)-4-(2-hydroxyethyl)homopiperazine-1-carboxyamide
N-(3,5-dichlorophenyl)-4-allylhomopiperazine-1-carboxyamide;
N-(3,5-dibromophenyl)-4-methylhomopiperazine-1-carboxyamide;

N-(3,5-dibromophenyl)-4-propylhomopiperazine-1-carboxyamide;
N-(3,5-dibromophenyl)-4-cyclopropylhomomethylpiperazine-1-carboxyamide;
N-(3,5-dibromophenyl)-4-(2-hydroxyethyl)homopiperazine-1-carboxyamide;
N-(3,5-dibromophenyl)-4-allylhomopiperazine-1-carboxyamide;
N-(3,5-dibromophenyl)-4-benzylhomopiperazine-1-carboxyamide;
N-(3,5-dimethylphenyl)-4-methylpiperazine-1-carboxyamide;
N-(3,5-dichlorophenyl)-4-methylpiperazine-1-carboxyamide;
N-(3,5-dichlorophenyl)-4-propylpiperazine-1-carboxyamide;
N-(3,5-dichlorophenyl)-4-cyclopropylmethylpiperazine-1-carboxyamide;
N-(3,5-dichlorophenyl)-4-(2-hydroxyethyl)piperazine-1-carboxyamide;
N-(3,5-dichlorophenyl)-4-allylpiperazine-1-carboxyamide;
N-(3,5-dibromophenyl)-4-methylpiperazine-1-carboxyamide;
N-(3,5-dibromophenyl)-4-propylpiperazine-1-carboxyamide;
N-(3,5-dibromophenyl)-4-cyclopropylmethylpiperazine-1-carboxyamide;
N-(3,5-dibromophenyl)-4-(2-hydroxyethyl)piperazine-1-carboxyamide;
N-(3,5-dibromophenyl)-4-allylpiperazine-1-carboxyamide;
N-(3,5-dibromophenyl)-4-benzylpiperazine-1-carboxyamide;
N-(3,5-difluorophenyl)-4-methylpiperazine-1-carboxyamide;
N-(3,5-difluorophenyl)-4-propylpiperazine-1-carboxyamide;
N-(3,5-difluorophenyl)-4-cyclopropylmethylpiperazine-1-carboxyamide;
N-(3,5-difluorophenyl)-4-(2-hydroxyethyl)piperazine-1-carboxyamide;
N-(3,5-difluorophenyl)-4-allylpiperazine-1-carboxyamide;
N-(3,5-difluorophenyl)-4-benzylpiperazine-1-carboxyamide;
1-allyl-1-methyl-4-(3,5-dimethylphenylcarbamoyl)piperazinium iodide;
1,1-dimethyl-4-(3,5-dimethylphenylcarbamoyl)piperazinium iodide;
1-(2-hydroxyethyl)-1-methyl-4-(3,5-dimethylphenylcarbamoyl)piperazinium iodide;
1,1-dimethyl-4-(3,5-dichlorophenylcarbamoyl)piperazinium iodide;
1-ethyl-1-methyl-4-(3,5-dichlorophenylcarbamoyl)piperazinium iodide;
1-propyl-1-methyl-4-(3,5-dichlorophenylcarbamoyl)piperazinium iodide;
1-allyl-1-methyl-4-(3,5-dichlorophenylcarbamoyl)piperazinium iodide;
1-(2-hydroxyethyl)-1-methyl-4-(3,5-dichlorophenylcarbamoyl)piperazinium iodide;
1-(2-hydroxyethyl)-1-methyl-4-(3,5-dichlorophenylcarbamoyl)piperazinium chloride;
1-(2-hydroxyethyl)-1-methyl-4-(3,5-dichlorophenylcarbamoyl)piperazinium bromide;
1-propyl-1-methyl-4-(3,5-dichlorophenylcarbamoyl)piperazinium bromide;
1-cyclopropylmethyl-1-methyl-4-(3,5-dichlorophenylcarbamoyl)piperazinium bromide;
1-benzyl-1-methyl-4-(3,5-dichlorophenylcarbamoyl)piperazinium bromide;
1,1-dimethyl-4-(3,5-dichlorophenylcarbamoyl)homopiperazinium iodide;
1-allyl-1-methyl-4-(3,5-dichlorophenylcarbamoyl)homopiperazinium iodide;
1-(2-hydroxyethyl)-1-methyl-4-(3,5-dichlorophenylcarbamoyl)homopiperazinium iodide;
1-(2-hydroxyethyl)-1-methyl-4-(3,5-dichlorophenylcarbamoyl)homopiperazinium chloride;
1-(2-hydroxyethyl)-1-methyl-4-(3,5-dichlorophenylcarbamoyl)homopiperazinium bromide;
1-propyl-1-methyl-4-(3,5-dichlorophenylcarbamoyl)homopiperazinium bromide;
1-cyclopropylmethyl-1-methyl-4-(3,5-dichlorophenylcarbamoyl)homopiperazinium bromide;
1-benzyl-1-methyl-4-(3,5-dichlorophenylcarbamoyl)homopiperazinium bromide;
1,1-dimethyl-4-(3-chlorophenylcarbamoyl)homopiperazinium iodide;
1-allyl-1-methyl-4-(3-chlorophenylcarbamoyl)homopiperazinium iodide;
1-(2-hydroxyethyl)-1-methyl-4-(3-chlorophenylcarbamoyl)piperazinium iodide;
1-allyl-1-methyl-4-(3-chlorophenylcarbamoyl)homopiperazinium iodide;
1,1-dimethyl-4-(2-methoxy-5-chlorophenylcarbamoyl)piperazinium iodide;
1-allyl-1-methyl-4-(2-methoxy-5-chlorophenylcarbamoyl)piperazinium iodide;
1-(2-hydroxyethyl)-1-methyl-4-(2-methoxy-5-chlorophenylcarbamoyl)piperazinium iodide;
1-allyl-1-methyl-4-(2-methoxy-5-chlorophenylcarbamoyl)homopiperazinium iodide;
1,1-dimethyl-4-(3-bromophenylcarbamoyl)piperazinium iodide;
1-allyl-1-methyl-4-(3-bromophenylcarbamoyl)piperazinium iodide;
1-(2-hydroxyethyl)-1-methyl-4-(3-bromophenylcarbamoyl)piperazinium iodide;
1-allyl-1-methyl-4-(3-bromophenylcarbamoyl)homopiperazinium iodide;
1,1-dimethyl-4-(3-fluorophenylcarbamoyl)piperazinium iodide;
1-allyl-1-methyl-4-(3-fluorophenylcarbamoyl)piperazinium iodide;
1-(2-hydroxyethyl)-methyl-4-(3-fluorophenylcarbamoyl)piperazinium iodide;
1,1-dimethyl-4-(3,5-difluorophenylcarbamoyl)piperazinium iodide;
1-allyl-1-methyl-4-(3,5-difluorophenylcarbamoyl)piperazinium iodide;
1-(2-hydroxyethyl)-methyl-4-(3,5-difluorophenylcarbamoyl)piperazinium iodide, and the like. However, the active ingredient of the serotonin 5-HT3 receptor agonist of the present invention is not limited to these examples.

The serotonin 5-HT3 receptor agonist of the present invention is preferably provided as a pharmaceutical composition containing a compound represented by the aforementioned general formula (1) or the general formula (2) or a physiologically acceptable salt thereof or a compound represented by the aforementioned general formula (3) as an active ingredient and one or more kinds of pharmaceutical additives as required. The aforementioned pharmaceutical composition can be administered to humans or mammals other than humans via either an oral or parenteral administration route (for example, intravenous administration, intramuscular administration, subcutaneous administration, drip infusion, transmucosal or percutaneous administration, intrarectal administration, inhalation, and the like). The aforementioned pharmaceutical composition can be prepared as a composition in an appropriate form depending on the administration route. More specifically, examples of pharmaceutical compositions suitable for oral administration include tablets, capsules, powders, granules, syrups, and the like. Examples of pharmaceutical compositions suitable as parenteral agents include injections for intravenous administration or intramuscular administration, drip infusions for intravenous administration, agents for intrarectal administration, oleaginous suppositories, aqueous suppositories, patches for transmucosal or percutaneous administration, inhalants, and the like. These various pharmaceutical compositions can be prepared in a conventional manner by using one or more kinds of usually used additives for pharmaceutical preparations such as excipients, disintegrating agents, binders, lubricants and colorants.

Examples of usable nontoxic excipients include, for example, lactose, glucose, corn starch, sorbit, crystalline cellulose, and the like. Examples of disintegrating agents include, for example, starch, sodium alginate, gelatin, calcium carbonate, calcium citrate, dextrin, and the like. Examples of binders include, for example, dimethylcellulose, polyvinyl alcohol, polyvinyl ether, methylcellulose, ethylcellulose, gum arabic, hydroxypropylcellulose, polyvinylpyrrolidone, and the like. Examples of lubricants include, for example, talc, magnesium stearate, polyethylene glycol, hydrogenated oil, and the like. For injections, buffers, pH modifiers, stabilizers, and the like can be added as required.

Although the content of the active ingredient in the pharmaceutical composition varies depending on the form of the pharmaceutical composition, the amount is usually about 0.05 to 50% by mass, preferably about 0.1 to 20% by mass, based on the total mass of the composition. Doses are suitably determined for individual patients by taking into account age, body weight, sexuality, type of disease, severity of symptom, and the like, and a usual daily dose for adults is 0.5 to 1000 mg, preferably 1 to 300 mg. The aforementioned dose can be administered once d day or several times per day as divided portions.

EXAMPLES

The present invention will be explained more specifically with reference to examples. However, the following explanations are given merely as examples and do not limit the scope of the present invention. Various modifications and alterations thereof are possible without departing from the scope of the invention. The NMR data mentioned in the examples are δ values obtained by 300 MHz NMR using TMS as the standard.

Example 1

N-(2-Methylphenyl)-4-methylpiperazine-1-carboxyamide

A solution of triphosgene (1.469 g, 4.95 mmol) in chloroform (10 ml) was added dropwise with a solution of 1-methylpiperazine (1.5 g, 15 mmol) in chloroform (10 ml) with stirring under ice cooling, and the mixture was stirred at room temperature for one hour. The resulting suspension of acid chloride was added dropwise with a solution of ortho-toluidine (1.071 g, 10 mmol) in chloroform (10 ml), and added with triethylamine (1.518 g, 15 mmol), and the mixture was refluxed for 12 hours. The reaction mixture was added to water to precipitate a diphenyl urea derivative, which was separated by filtration. Then, the aqueous layer was made sufficiently acidic with 10% hydrochloric acid and washed with dichloromethane. The aqueous layer was made sufficiently basic with 20% aqueous potassium carbonate and extracted with dichloromethane. The organic layer washed with a small volume of water and dried over anhydrous sodium sulfate, and then the solvent was evaporated under reduced pressure. The resulting mixture was recrystallized from ethyl acetate/n-hexane to obtain colorless acicular crystals. Melting point: 148-149° C.

$^1$H-NMR (CDCl$_3$): 2.25 (3H, s), 2.34 (3H, s), 2.45 (4H, t, J=5 Hz), 3.52 (4H, t, J=5 Hz), 6.11 (1H, brs), 7.01-7.63 (4H, m).

Example 2

N-(3-Methylphenyl)-4-methylpiperazine-1-carboxyamide

By using meta-toluidine, the title compound was obtained in the same manner as that used in Example 1. Melting point: 88-89° C.

$^1$H-NMR (CDCl$_3$): 2.30 (3H, s), 2.32 (3H, s), 2.44 (4H, t, J=5 Hz), 3.51 (4H, t, J=5 Hz), 6.41 (1H, brs), 7.08-7.27 (4H, m).

Example 3

N-(3,5-Dimethylphenyl)-4-methylpiperazine-1-carboxyamide

By using 3,5-dimethylaniline, the title compound was obtained in the same manner as that used in Example 1. Melting point: 81-82° C.

$^1$H-NMR (CDCl$_3$): 2.32 and 2.33 (9H, s), 2.46 (4H, t, J=5 Hz), 3.44 (4H, t, J=5 Hz), 6.31 (1H, brs), 6.99 (2H, s), 7.03 (1H, s).

Example 4

N-(2-Hydroxyphenyl)-4-methylpiperazine-1-carboxyamide

By using 2-aminophenol, the title compound was obtained in the same manner as that used in Example 1. Melting point: 144-146° C.

$^1$H-NMR (DMSO-d$_6$): 2.19 (3H, s), 2.31 (4H, t, J=5 Hz), 3.43 (4H, t, J=5 Hz), 6.74-7.40 (4H, m), 7.96 (1H, brs), 9.71 (1H, brs).

Example 5

N-(5-Chloro-2-hydroxyphenyl)-4-methylpiperazine-1-carboxyamide

By using 4-chloro-2-aminophenol, the title compound was obtained in the same manner as that used in Example 1. Melting point: 134-135° C.

$^1$H-NMR (DMSO-d$_6$): 2.19 (3H, s), 2.31 (4H, t, J=5 Hz), 3.42 (4H, t, J=5 Hz), 6.80-6.89 (3H, m), 7.61 (1H, d, J=3 Hz), 7.87 (1H, brs).

Example 6

N-(3,5-Dichlorophenyl)-4-methylpiperazine-1-carboxyamide 3,5-Dichlorobenzoic acid (3.82 g, 20 mmol) was added with thionyl chloride (24.48 g, 205 mmol), and the mixture was refluxed for 6 hours. After completion of the reaction, excess thionyl chloride was evaporated, and the residue was dried overnight in a desiccator. The resulting acid chloride was used for the subsequent reaction as it was. A suspension of sodium azide (1.78 g, 35.6 mmol) in acetone (15 ml) was added dropwise with a solution of 3,5-dichlorobenzoyl chloride (3.87 g, 18.48 mmol) in acetone (15 ml) with stirring under ice cooling, and the mixture was stirred with ice cooling for 1 hour. The reaction mixture was added with water, and the deposited crystals were collected by filtration and dried under reduced pressure to obtain an acid azide compound. A solution of the resulting 3,5-dichlorobenzoyl azide (0.54 g, 2.5 mmol) in toluene (5 ml) was heated at 60 to 70° C. until generation of nitrogen ceased. After effervescence ceased, the mixture was added with a solution of 1-methylpiperazine (0.275 g, 2.75 mmol) in toluene (3 ml), and the mixture was stirred for 5 minutes. The reaction mixture was added with water, and the aqueous layer was made sufficiently acidic with 10% hydrochloric acid and washed with dichloromethane. Then, the aqueous layer was made sufficiently basic with 20% aqueous potassium carbonate and extracted with dichloromethane. The organic layer washed with a small volume of water and dried over anhydrous sodium sulfate, and then the solvent was evaporated under reduced pressure. The resulting mixture was recrystallized from ether/n-hexane for purification to obtain colorless prism crystals. Melting point: 184-185° C.

$^1$H-NMR (CDCl$_3$): 2.32 (3H, s), 2.43 (4H, t, J=5 Hz), 3.50 (4H, t, J=5 Hz), 6.50 (1H, brs), 7.00 (1H, s), 7.31-7.32 (2H, s).

Example 7

N-(3,5-Dichlorophenyl)-4-(2-hydroxyethyl)piperazine-1-carboxyamide

By using 1-piperazineethanol, the title compound was obtained in the same manner as that used in Example 6. Melting point: 95-96° C.

$^1$H-NMR (CDCl$_3$): 2.55-2.62 (6H, m), 3.50 (4H, t, J=5 Hz), 3.66 (2H, t, J=5 Hz), 6.36 (1H, brs), 7.02 (1H, s), 7.33-7.35 (2H, s).

Example 8

1-Allyl-1-methyl-4-(3,5-dimethylphenylcarbamoyl) piperazinium iodide

A solution of N-(3,5-dimethylphenyl)-4-methylpiperazine-1-carboxyamide (0.165 g, 0.67 mmol) obtained in Example 3 in tetrahydrofuran (5 ml) was added dropwise with a solution of allyl iodide (0.562 g, 3.35 mmol) in tetrahydrofuran (5 ml) with stirring under ice cooling. The mixture was stirred at room temperature for 3 hours, and the deposited crystals were collected by filtration and recrystallized from methanol/acetone to obtain colorless acicular crystals. Melting point: 235-236° C.

$^1$H-NMR (CD$_3$OD): 3.18 (3H, s), 3.51-3.54 (4H, m), 3.78-3.84 (2H, m), 4.03-4.15 (4H, m), 5.75-5.80 (2H, m), 6.09-6.15 (1H, m), 6.99 (2H, s), 7.03 (1H, s).

Example 9

1,1-Dimethyl-4-(3,5-dichlorophenylcarbamoyl)piperazinium iodide

A solution of N-(3,5-dichlorophenyl)-4-methylpiperazine-1-carboxyamide (0.193 g, 0.67 mmol) obtained in Example 6 in tetrahydrofuran (5 ml) was added dropwise with a solution of methyl iodide (0.472 g, 3.35 mmol) in tetrahydrofuran (5 ml) with stirring under ice cooling. The reaction mixture was stirred at room temperature for 3 hours, and the deposited crystals were collected by filtration and recrystallized from methanol/acetone to obtain colorless acicular crystals. Melting point: 208-209° C.

$^1$H-NMR (CD$_3$OD): 3.26 (6H, s), 3.52 (4H, t, J=5 Hz), 3.89 (4H, brs), 7.08 (1H, t, J=2 Hz), 7.32 (2H, d, J=2 Hz).

Example 10

1-Allyl-1-methyl-4-(3,5-dichlorophenylcarbamoyl) piperazinium iodide

By using N-(3,5-dichlorophenyl)-4-methylpiperazine-1-carboxyamide obtained in Example 6, the title compound was obtained in the same manner as that used in Example 8. Melting point: 219-220° C.

$^1$H-NMR (CD$_3$OD): 3.18 (3H, s), 3.51-3.54 (4H, m), 3.78-3.84 (2H, m), 4.03-4.15 (4H, m), 5.75-5.80 (2H, m), 6.09-6.15 (1H, m), 7.08 (1H, t, J=2 Hz), 7.32 (2H, d, J=2 Hz).

Example 11

1-(2-Hydroxyethyl)-1-methyl-4-(3,5-dichlorophenyl-carbamoyl)-piperazinium iodide By using N-(3,5-dichlorophenyl)-4-(2-hydroxyethyl)piperazine-1-carboxyamide obtained in Example 7, the title compound was obtained in the same manner as that used in Example 9. Melting point: 194-196° C.

$^1$H-NMR (CD$_3$OD): 3.31 (3H, s), 3.56-3.67 (6H, m), 3.88-3.95 (4H, m), 4.06 (2H, brs), 7.07 (1H, t, J=2 Hz), 7.32 (2H, d, J=2 Hz).

Example 12

1-Propyl-1-methyl-4-(3,5-dichlorophenylcarbamoyl) piperazinium bromide

A solution of N-(3,5-dichlorophenyl)-4-methylpiperazine-1-carboxyamide (0.2 g, 0.69 mmol) obtained in Example 6 in tetrahydrofuran (5 ml) was stirred with ice cooling, and added dropwise with a solution of propyl bromide (0.42 g, 3.45 mmol) in tetrahydrofuran (5 ml), and the mixture was stirred at 60° C. for 12 hours. The deposited crystals were collected by filtration and recrystallized from methanol/ether to obtain colorless acicular crystals. Melting point: 249-250° C.

$^1$H-NMR (CD$_3$OD): 1.05 (3H, t, J=7 Hz), 1.81-1.89 (2H, m), 3.19 (3H, s), 3.40-3.52 (2H, m), 3.50-3.53 (4H, m), 3.75-3.84 and 3.99-4.04 (4H, m), 7.08 (1H, s), 7.46 (2H, s).

Example 13

1-Cyclopropylmethyl-1-methyl-4-(3,5-dichlorophenylcarbamoyl)-piperazinium bromide A solution of N-(3,5-dichlorophenyl)-4-methylpiperazine-1-carboxyamide (0.2 g, 0.69 mmol) obtained in Example 6 in tetrahydrofuran (5 ml) was added dropwise with a solution of cyclopropylmethyl bromide (0.465 g, 3.45 mmol) in tetrahydrofuran (5 ml) with stirring under ice cooling, and the mixture was refluxed by heating for 12 hours. The deposited crystals were collected by filtration and recrystallized from methanol/dichloromethane to obtain colorless acicular crystals. Melting point: 218-219° C.

¹H-NMR (CD₃OD): 0.48-0.53 and 0.83-0.90 (4H, m), 1.22-1.27 (1H, m), 3.28 (3H), 3.42 (2H, d, J=7 Hz), 3.57 (4H, brs), 3.76-3.80 and 4.03-4.08 (4H, m), 7.08 (1H, s), 7.47 (2H, s).

Example 14

1-Benzyl-1-methyl-4-(3,5-dichlorophenylcarbamoyl) piperazinium bromide

A solution of N-(3,5-dichlorophenyl)-4-methylpiperazine-1-carboxyamide (0.2 g, 0.69 mmol) obtained in Example 6 in tetrahydrofuran (5 ml) was added dropwise with a solution of benzyl bromide (0.589 g, 3.45 mmol) in tetrahydrofuran (5 ml) with stirring under ice cooling, and the mixture was stirred at room temperature for 12 hours. The deposited crystals were collected by filtration and recrystallized from methanol/tetrahydrofuran to obtain colorless acicular crystals. Melting point: 242-244° C.
¹H-NMR (CD₃OD): 3.13 (3H, s), 3.45-3.78 (6H, m), 4.16-4.21 (2H, m), 4.68 (2H, s) 7.08 (1H, s), 7.47 (2H, s) 7.55-7.61 (5H, m).

Example 15

1,1-Dimethyl-4-(3-chlorophenylcarbamoyl)piperazinium iodide a) By using 3-chlorobenzoic acid, N-(3-chlorophenyl)-4-methylpiperazine-1-carboxyamide was obtained in the same manner as that used in Example 6. Melting point: 104-105° C.
¹H-NMR (CDCl₃): 2.33 (3H, s), 2.45 (4H, t, J=5 Hz), 3.51 (4H, t, J=5 Hz), 6.35 (1H, brs), 6.98-7.26 (4H, m).
b) By using N-(3-chlorophenyl)-4-methylpiperazine-1-carboxyamide obtained in (a), the title compound was obtained in the same manner as that used in Example 9. Melting point: 209-211° C.
¹H-NMR (CD₃OD): 3.27 (6H, s), 3.53 (4H, t, J=5 Hz), 3.90 (4H, brs), 6.95-7.04 (2H, m), 7.75 (1H, d, J=2 Hz).

Example 16

1-Allyl-1-methyl-4-(3-chlorophenylcarbamoyl)piperazinium iodide

By using N-(3-chlorophenyl)-4-methylpiperazine-1-carboxyamide obtained in Example 15, (a), the title compound was obtained in the same manner as that used in Example 8. Melting point: 229-230° C.
¹H-NMR (CD₃OD): 3.18 (3H, s), 3.51-3.54 (4H, m), 3.78-3.84 (2H, m), 4.03-4.15 (4H, m), 5.75-5.80 (2H, m), 6.09-6.15 (1H, m), 7.02-7.05 (1H, m), 7.22-7.30 (1H, m), 7.55 (1H, s).

Example 17

1-(2-Hydroxyethyl)-1-methyl-4-(3-chlorophenylcarbamoyl)piperazinium iodide a) By using 3-chlorobenzoic acid and 1-piperazineethanol, N-(3-chlorophenyl)-4-(2-hydroxyethyl)piperazine-1-carboxyamide was obtained in the same manner as that used in Example 6.
¹H-NMR (CDCl₃): 2.55-2.62 (6H, m), 3.51-3.54 (4H, m), 3.66 (2H, t, J=5 Hz), 6.41 (1H, brs), 7.00-7.03 (1H, m), 7.19-7.26 (2H, m), 7.46 (1H, s).

b) By using N-(3-chlorophenyl)-4-(2-hydroxyethyl)piperazine-1-carboxyamide obtained in (a), the title compound was obtained in the same manner as that used in Example 9. Melting point: 169-170° C.
¹H-NMR (CD₃OD): 3.31 (3H, s), 3.56-3.67 (6H, m), 3.88-3.95 (4H, m), 4.06 (2H, brs), 7.01-7.28 (3H, m), 7.55 (1H, s).

Example 18

1-Allyl-1-methyl-4-(3-chlorophenylcarbamoyl)homopiperazinium iodide a) By using 3-chlorobenzoic acid and 1-methylhomopiperazine, N-(3-chlorophenyl)-4-methylhomopiperazine-1-carboxyamide was obtained in the same manner as that used in Example 7. Melting point: 117-118° C.
¹H-NMR (CDCl₃): 1.96-2.00 (2H, m), 2.38 (3H, s), 2.59-2.69 (4H, m), 3.56-3.68 (4H, m), 6.33 (1H, brs), 6.98-7.01 (1H, m), 7.16-7.22 (2H, m), 7.51 (1H, s).
b) By using N-(3-chlorophenyl)-4-methylhomopiperazine-1-carboxyamide obtained in (a), the title compound was obtained in the same manner as that used in Example 9. Melting point: 185-186° C.
¹H-NMR (CD₃OD): 2.34 (2H, brs), 3.14 (3H, s), 3.58-3.63 (4H, m), 3.68 (2H, t, J=6 Hz), 3.89-4.14 (4H, m), 5.73-5.78 (2H, m), 6.08-6.16 (1H, m), 7.01-7.05 (1H, m), 7.21-7.33 (12, m), 7.57 (1H, t, J=2 Hz).

Example 19

1,1-Dimethyl-4-(2-methoxy-5-chlorophenylcarbamoyl)piperazinium iodide a) By using 5-chloro-2-methoxybenzoic acid and 1-methylpiperazine, N-(5-chloro-2-methoxyphenyl)-4-methylpiperazine-1-carboxyamide was obtained in the same manner as that used in Example 6. Melting point: 80-82° C.
¹H-NMR (CDCl₃): 2.33 (3H, s), 2.45 (4H, t, J=5 Hz), 3.52 (4H, t, J=5 Hz), 3.82 (3H, s), 6.73-6.91 (3H, m), 7.09 (1H, brs), 8.24 (1H, d, J=3 Hz).
b) By using N-(5-chloro-2-methoxyphenyl)-4-methylpiperazine-1-carboxyamide obtained in (a), the title compound was obtained in the same manner as that used in Example 9. Melting point: 208-210° C.
¹H-NMR (CD₃OD): 3.27 (6H, s), 3.53 (4H, t, J=5 Hz), 3.87 (3H, s), 3.90 (4H, brs), 6.95-7.04 (2H, m), 7.75 (1H, d, J=2 Hz).

Example 20

1-Allyl-1-methyl-4-(2-methoxy-5-chlorophenylcarbamoyl)piperazinium iodide

By using N-(5-chloro-2-methoxyphenyl)-4-methylpiperazine-1-carboxyamide obtained in Example 19, (a), the title compound was obtained in the same manner as that used in Example 8. Melting point: 224-225° C.
¹H-NMR (CD₃OD): 3.18 (3H, s), 3.51-3.52 (4H, m), 3.81-3.85 (2H, m), 3.87 (3H, s), 4.02-4.05 (2H, m) 4.15 (2H, d, J=7 Hz), 5.75-5.80 (2H, m), 6.08-6.17 (1H, m), 7.07-7.07 (2H, m), 7.75 (1H, s).

Example 21

1-(2-Hydroxyethyl)-1-methyl-4-(2-methoxy-5-chlorophenylcarbamoyl)-piperazinium iodide a) By using 5-chloro-2-methoxybenzoic acid and 1-piperazineethanol, N-(5-chloro-2-methoxyphenyl)-4-(2-hydroxyethyl)piperazine-1-carboxyamide was obtained in the same manner as that used in Example 6. Melting point: 87-88° C.

$^1$H-NMR (CDCl$_3$): 2.54-2.62 (6H, m), 3.51-3.54 (4H, m), 3.66 (2H, t, J=5 Hz), 3.87 (3H, s), 6.73 (1H, d, J=8 Hz), 6.92 (1H, dd, J=8 and 3 Hz), 7.10 (1H, brs), 8.22 (1H, d, J=3 Hz).

b) By using N-(5-chloro-2-methoxyphenyl)-4-(2-hydroxyethyl)piperazine-1-carboxyamide obtained in (a), the title compound was obtained in the same manner as that used in Example 9. Melting point: 149-150° C.

$^1$H-NMR (CD$_3$OD): 3.32 (3H, s), 3.56-3.74 (6H, m), 3.87 (3H, s), 3.91-3.94 (4H, m), 4.06 (2H, brs), 6.95-7.06 (3H, m), 7.76 (1H, s).

Example 22

1-Allyl-1-methyl-4-(2-methoxy-5-chlorophenylcarbamoyl)-homopiperazinium iodide a) By using 5-chloro-2-methoxybenzoic acid and 1-methylhomopiperazine, N-(5-chloro-2-methoxyphenyl)-4-methylhomopiperazine-1-carboxyamide was obtained in the same manner as that used in Example 6. Melting point: 90-91° C.

$^1$H-NMR (CDCl$_3$): 1.97-2.01 (2H, m), 2.38 (3H, s), 2.59-2.69 (4H, m), 3.57-3.69 (4H, m), 3.86 (3H, s), 6.72 (1H, d, J=8 Hz), 6.88 (1H, dd, J=8 and 3 Hz), 7.07 (1H, brs), 8.27 (1H, d, J=3 Hz).

b) By using N-(5-chloro-2-methoxyphenyl)-4-methylhomopiperazine-1-carboxyamide obtained in (a), the title compound was obtained in the same manner as that used in Example 8. Melting point: 169-171° C.

$^1$H-NMR (CD$_3$OD): 2.34 (2H, brs), 3.14 (3H, s), 3.78-3.63 (4H, m), 3.68 (2H, t, J=6 Hz), 3.88 (3H, s), 3.91-4.13 (4H, m), 5.73-5.78 (2H, m), 6.08-6.16 (1H, m), 6.95-7.06 (2H, m), 7.84 (1H, d, J=2 Hz).

Example 23

1,1-Dimethyl-4-(3-bromophenylcarbamoyl)piperazinium iodide a) By using 3-bromobenzoic acid and 1-methylpiperazine, N-(3-bromophenyl)-4-methylpiperazine-1-carboxyamide was obtained in the same manner as that used in Example 6. Melting point: 108-109° C.

$^1$H-NMR (CDCl$_3$): 2.33 (3H, s), 2.44 (4H, t, J=5 Hz), 3.51 (4H, t, J=5 Hz), 6.37 (1H, brs), 7.12-7.27 (3H, m), 7.60 (1H, brs).

b) By using N-(3-bromophenyl)-4-methylpiperazine-1-carboxyamide obtained in (a), the title compound was obtained in the same manner as that used in Example 9. Melting point: 215-218° C.

$^1$H-NMR (CD$_3$OD): 3.26 (6H, s), 3.52 (4H, t, J=5 Hz), 3.89 (4H, brs), 7.17-7.34 (3H, m), 7.69 (1H, s).

Example 24

1-Allyl-1-methyl-4-(3-bromophenylcarbamoyl)piperazinium iodide

By using N-(3-bromophenyl)-4-methylpiperazine-1-carboxyamide obtained in Example 23, (a), the title compound was obtained in the same manner as that used in Example 8. Melting point: 220-223° C.

$^1$H-NMR (CD$_3$OD): 3.18 (3H, s), 3.50-3.54 (4H, m), 3.76-3.85 (2H, m), 4.02-4.07 (2H, m), 4.15 (2H, d, J=7 Hz), 5.74-5.80 (2H, m), 6.08-6.17 (1H, m), 7.18-7.20 (2H, m), 7.31-7.35 (1H, m), 7.70 (1H, s).

Example 25

1-(2-Hydroxyethyl)-1-methyl-4-(3-bromophenylcarbamoyl)piperazinium iodide a) By using 3-bromobenzoic acid and 1-piperazineethanol, N-(3-bromophenyl)-4-(2-hydroxyethyl)piperazine-1-carboxyamide was obtained in the same manner as that used in Example 6. Melting point: 110-112° C.

$^1$H-NMR (CDCl$_3$): 2.52-2.61 (6H, m), 3.50-3.53 (4H, m), 3.66 (2H, t, J=5 Hz), 6.44 (1H, brs), 7.10-7.28 (3H, m), 7.59 (1H, s).

b) By using N-(3-bromophenyl)-4-(2-hydroxyethyl)piperazine-1-carboxyamide obtained in (a), the title compound was obtained in the same manner as that used in Example 9. Melting point: 163-164° C.

$^1$H-NMR (CD$_3$OD): 3.31 (3H, s), 3.56-3.67 (6H, m), 3.88-3.95 (4H, m), 4.06 (2H, brs), 7.17-7.34 (3H, m), 7.69 (1H, s).

Example 26

1-Allyl-1-methyl-4-(3-bromophenylcarbamoyl)homopiperazinium iodide a) By using 3-bromobenzoic acid and 1-methylhomopiperazine, N-(3-bromophenyl)-4-methylhomopiperazine-1-carboxyamide was obtained in the same manner as that used in Example 6. Melting point: 123-124° C.

$^1$H-NMR (CDCl$_3$): 1.97-2.00 (2H, m), 2.38 (3H, s), 2.60-2.65 (4H, m), 3.56-3.68 (4H, m), 6.29 (1H, brs), 7.12-7.30 (3H, m), 7.64 (1H, s).

b) By using N-(3-bromophenyl)-4-methylhomopiperazine-1-carboxyamide obtained in (a), the title compound was obtained in the same manner as that used in Example 8. Melting point: 172-174° C.

$^1$H-NMR (CD$_3$OD): 2.34 (2H, brs), 3.14 (3H, s), 3.58-3.63 (4H, m), 3.68 (2H, t, J=6 Hz), 3.89-4.14 (4H, m), 5.73-5.78 (2H, m), 6.08-6.16 (1H, m), 7.17-7.37 (3H, m), 7.72 (1H, brs).

Example 27

1,1-Dimethyl-4-(3-fluorophenylcarbamoyl)piperazinium iodide a) By using 3-fluorobenzoic acid and 1-methylpiperazine, N-(3-fluorophenyl)-4-methylpiperazine-1-carboxyamide was obtained in the same manner as that used in Example 6. Melting point: 122-123° C.

$^1$H-NMR (CDCl$_3$): 2.33 (3H, s), 2.45 (4H, t, J=5 Hz), 3.51 (4H, t, J=5 Hz), 6.39 (1H, brs), 6.72-6.80 (1H, m), 6.97-7.32 (3H, m).

b) By using N-(3-fluorophenyl)-4-methylpiperazine-1-carboxyamide obtained in (a), the title compound was obtained in the same manner as that used in Example 9. Melting point: 193-195° C.

$^1$H-NMR (CD$_3$OD): 3.27 (6H, s), 3.54 (4H, t, J=5 Hz), 3.92 (4H, brs), 6.72-6.79 (1H, m), 7.13-7.34 (3H, m).

Example 28

1,1-Dimethyl-4-(3,5-difluorophenylcarbamoyl)piperazinium iodide a) By using 3,5-difluorobenzoic acid and 1-methylpiperazine, N-(3,5-difluorophenyl)-4-methylpiperazine-1-carboxyamide was obtained in the same manner as that used in Example 6. Melting point: 150-151° C.

¹H-NMR (CDCl₃): 2.33 (3H, s), 2.44 (4H, t, J=5 Hz), 3.51 (4H, t, J=5 Hz), 6.39-6.48 (2H, m), 6.95-6.99 (2H, m).

b) By using N-(3,5-difluorophenyl)-4-methylpiperazine-1-carboxyamide obtained in (a), the title compound was obtained in the same manner as that used in Example 9. Melting point: 225-228° C.

¹H-NMR (CD₃OD): 3.27 (6H, s), 3.53 (4H, t, J=5 Hz), 3.90 (4H, brs), 6.55-6.61 (1H, m), 7.09-7.13 (2H, m).

Example 29

1-(2-Hydroxyethyl)-1-methyl-4-(3,5-dichlorophenyl-carbamoyl)-piperazinium chloride Amberlite IRA-400 resin (100 ml), a strongly basic ion exchange resin, was added with 1 N aqueous sodium hydroxide (200 ml), left for 30 minutes, then collected by filtration through a glass filter and washed with distilled water. Then, the resin was added with 1 N aqueous hydrochloric acid (200 ml), left for one hour, then collected by filtration through a glass filter and washed with distilled water until pH of the filtrate became neutral to obtain an ion exchanger. 1-(2-Hydroxyethyl)-1-methyl-4-(3,5-dichlorophenylcarbamoyl)piperazinium iodide obtained in Example 11 was subjected to ion exchange chromatography (methanol:water=10:1) using the resulting ion exchanger to obtain the title compound. Melting point: 154-156° C.

Example 30

1-(2-Hydroxyethyl)-1-methyl-4-(3,5-dichlorophenyl-carbamoyl)-piperazinium bromide By using 1 N aqueous hydrobromic acid, the title compound was obtained in the same manner as that used in Example 29. Melting point: 159-161° C.

Test Example 1

Serotonin 5-HT3 Receptor Binding Affinity

Serotonin 5-HT3 receptor binding affinities of the urea derivatives of the present invention and typical compounds among known urea derivatives, N-phenyl-4-methylpiperazine-1-carboxyamide (A), N-(4,5-dichlorophenyl)-4-methylppiperazine-1-carboxyamide (B), N-(3,5-trifluoromethylphenyl)-4-methylpiperazine-1-carboxyamide (C), N-(3-fluorophenyl)-4-methylpiperazine-1-carboxyamide (D) and N-(5-chloro-2-methoxyphenyl)-(4-tert-butyloxycarbonylpiperazine)-1-carboxyamide (E), were determined by the following method, and the results are shown in Table 1. The test compounds of the present invention are mentioned with the example numbers.

According to the method of Boess et al. (Neuropharmacology, 36, 637-647, 1997), affinities were examined by using a membrane fraction obtained from HEK-293 cells and a ligand selective to the serotonin 5-HT3 receptor, [3H]-GR-65630 [3-(5-methyl-1H-imidazol-4-yl)-1-(1-methyl-1H-indol-3-yl)-1-propanone] on the basis of inhibitory actions of the test compounds on the specific binding to GR-65630 as an index. The results of the test for inhibition of binding to the serotonin 5-HT3 receptor are shown in Table 1. As clearly understood from the results shown in the table, the compounds of the present invention have a more potent binding action on the serotonin 5-HT3 receptor than the known urea derivatives having a similar structure.

TABLE 1

Serotonin 5-HT3 receptor binding affinity

| Compound | [3H]-GR65630 binding inhibition rate at 1 µM |
|---|---|
| Compound of Example 5 | 81% |
| Compound of Example 6 | 101% |
| Compound of Example 9 | 104% |
| Compound of Example 10 | 105% |
| Compound of Example 11 | 104% |
| Compound of Example 12 | 98% |
| Compound of Example 13 | 98% |
| Compound of Example 14 | 96% |
| Compound of Example 19 | 94% |
| Compound of Example 20 | 92% |
| Compound of Example 21 | 98% |
| A | 1% |
| B | 22% |
| C | 2% |
| D | 28% |
| E | 5% |

Test Example 2

Test for Serotonin 5-HT3 Receptor Partially Activating Action

The serotonin 5-HT3 receptor antagonistic action and the serotonin 5-HT3 receptor activating action of 1-(2-hydroxyethyl)-1-methyl-4-(3,5-dichlorophenylcarbamoyl)piperazinium iodide as the compound of the present invention were determined according to the method of Butler et al. (Br. J. Pharmacol, 94, 397-412, 1988). The results are shown in Table 2.

About 30-mm longitudinal muscle samples were prepared from the ileums of male or female Hartley guinea pigs (325±25 g). Each sample was hung down in a Magnus tube filled with 10 ml of Krebs solution (pH 7.4, 32° C.) with ventilation of a mixed gas (95% $O_2$, 5% $CO_2$), and loaded with a tension of 1 g, and contractile responses were measured isometrically. The serotonin 5-HT3 receptor activating action of the test compound was represented in terms of a relative value obtained by comparison of the contraction obtained by adding 2.6 µM of serotonin 5-HT to the sample and the contraction of 50% or more obtained within 5 minutes as a percentage based on the maximum contraction. The serotonin 5-HT3 receptor antagonistic action of the test compound was obtained from the contraction suppression rate obtained by adding serotonin 5-HT to the sample.

TABLE 2

Test for serotonin 5-HT3 receptor activating action

| Concentration | Activating action | Antagonistic action |
|---|---|---|
| 100 µM | 23% | 36% |
| 30 µM | 31% | 27% |
| 10 µM | 14% | 37% |
| 3 µM | 4% | 30% |
| 1 µM | 0% | 15% |

It was confirmed that 1-(2-hydroxyethyl)-1-methyl-4-(3,5-dichlorophenylcarbamoyl)piperazinium iodide as the compound of the present invention was a superior serotonin 5-HT3 receptor agonist having both the serotonin 5-HT3 receptor antagonistic action and the serotonin 5-HT3 receptor activating action. Therefore, the compound of the present invention is effective as a receptor agonist having a serotonin 5-HT3 receptor partially activating action, and useful as a medicament based on these actions.

Test Example 3

Antiemetic Action on Cisplatin-Induced Emesis in Dogs

Actions on cisplatin-induced emesis in beagles of 1-(2-hydroxyethyl)-1-methyl-4-(3,5-dichlorophenylcarbamoyl)piperazinium bromide as the compound of the present invention and 5-chloro-2-(1-homopiperazinyl)-7-methylbenzooxazole (F) (International Publication WO00/31073), which is a benzoxazole derivative having a chemical structure similar to that of the novel urea derivative of the present invention among the known serotonin 5-HT3 receptor partially activating agents, were determined by the following method. The results are shown in Table 3. The compound of the present invention is mentioned with the example number.

After starvation for 16 hours from one day before the day of the test, beagles (each group consisted of two dogs) were given 300 g of feed pellets and intravenously received cisplatin at a dose of 3 mg/kg 30 minutes later. The test compound was intravenously given 30 minutes before the administration of cisplatin, and frequency and time of emesis were monitored over 6 hours.

TABLE 3

Antiemetic action on emesis induced by cisplatin

| Compound group | Animal No. | Dose (mg/kg) | Number of emesis 0 to 120 (minute) | Number of emesis 121 to 360 (minute) | Time of initial occurrence (minute) |
|---|---|---|---|---|---|
| Control | 1 | — | 4 | 29 | 96 |
| | 2 | — | 1 | 21 | 120 |
| F | 3 | 0.5 | 8 | 6 | 79 |
| | 4 | 0.5 | 14 | 15 | 88 |
| Example 30 | 5 | 0.5 | 0 | 1 | 165 |
| | 6 | 0.5 | 0 | 0 | — |

As clearly understood from the results of the aforementioned test, 1-(2-hydroxyethyl)-1-methyl-4-(3,5-dichlorophenylcarbamoyl)piperazinium bromide as the compound of the present invention (Example 30) effectively suppressed the cisplatin-induced emesis in dogs. It is reported that cisplatin-induced emesis occurs 90 minutes after administration (Folia Pharmacol. Jpn., 108, 233-242, 1996), whilst emesis occurred within 90 minutes after the administration when the known benzoxazole derivative (F) was administered. This result can be understood that the benzoxazole derivative having the serotonin 5-HT3 receptor activating action easily passed through the blood-brain barrier, as being a highly lipid-soluble substance having a low molecular weight, and stimulated the area postrema of the medulla oblongata including the emesis center. Whilst, as for the compound of the present invention, no emesis was observed at the initial stage of the administration thereof, although the compound has the serotonin 5-HT3 receptor activating action, which revealed that the compound has no action on the central nerve system. This result can be understood that the compound of the present invention as a quaternary salt did not pass through the blood-brain barrier.

INDUSTRIAL APPLICABILITY

A serotonin 5-HT3 receptor agonist containing the compound represented by the aforementioned general formula (1) or (2) or a physiologically acceptable salt thereof or the compound represented by the aforementioned general formula (3) as an active ingredient has both a serotonin 5-HT3 receptor antagonistic action and a serotonin 5-HT3 receptor activating action, and is useful as a medicament for prophylactic and/or therapeutic treatment of a disease associated with the serotonin 5-HT3 receptor, for example, emesis caused by anticancer agents such as cisplatin or radiation irradiation, nausea or emesis in kinetosis such as motion sickness, gastrointestinal motility disorders, irritable bowel syndrome, headache, neuralgia, anxiety symptoms, depression, mental diseases, diarrhea, constipation, and the like as a potent serotonin 5-HT3 receptor agonist with reduced adverse reactions.

The invention claimed is:

1. A compound represented by the general formula (3):

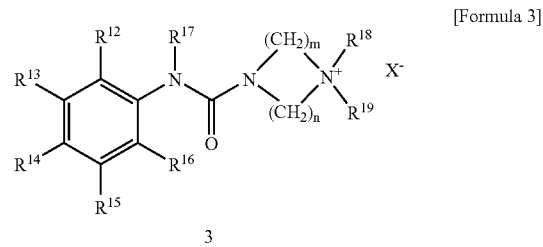

[Formula 3]

wherein $R^{12}$, $R^{13}$, $R^{14}$, $R^{15}$ and $R^{16}$ may be the same or different, and represent hydrogen atom, a halogen atom, a lower alkoxy group, trifluoromethyl group, a substituted or unsubstituted lower alkyl group, a substituted or unsubstituted lower alkenyl group, or a substituted or unsubstituted amino group, any two groups among $R^{12}$, $R^{13}$, $R^{14}$, $R^{15}$ and $R^{16}$ may bind to each other to form a cyclic structure (the cyclic structure is a 5- to 7-membered cyclic structure consisting only of carbon atoms or a 5- to 7-membered cyclic structure consisting of carbon atoms and one or two hetero atoms, and may have one or more the same or different substituents on the ring), $R^{17}$ represents hydrogen atom, a substituted or unsubstituted lower alkyl group, or a substituted or unsubstituted lower alkenyl group, $R^{18}$ and $R^{19}$ may be the same or different, and represent a substituted or unsubstituted lower alkyl group, a lower alkenyl group, or an aralkyl group, $X^-$ represents a physiologically acceptable anion species, and m and n may be the same and different, and represent an integer of 1 to 3.

2. A serotonin 5-HT3 receptor agonist comprising the compound represented by the general formula (3) according to claim 1 as an active ingredient.

* * * * *